United States Patent [19]

Sheedy

[11] 4,222,639

[45] Sep. 16, 1980

[54] APPARATUS AND SYSTEM FOR ANALYZING FIXATION DISPARITY

[76] Inventor: James E. Sheedy, 126 Aldrich Rd., Columbus, Ohio 43214

[21] Appl. No.: 956,403

[22] Filed: Oct. 31, 1978

[51] Int. Cl.$^3$ .............................................. A61B 3/08
[52] U.S. Cl. ........................................ 351/4; 351/32; 351/36; 351/37
[58] Field of Search ..................... 351/1, 4, 32, 36, 37, 351/39, 25

[56] References Cited

U.S. PATENT DOCUMENTS

| | | | |
|---|---|---|---|
| 1,292,671 | 1/1919 | Allen et al. | 351/4 |
| 1,946,925 | 2/1934 | Ames, Jr. | 351/1 |
| 2,126,713 | 8/1938 | Ames, Jr. et al. | 351/39 X |
| 3,486,813 | 12/1969 | Johnston | 351/39 X |

OTHER PUBLICATIONS

J. Sheedy et al., "Phoria . . .," *Am. J. Optom & Phys. Optics*, vol. 54, No. 7, Jul. 1977 (pp. 474–478).
R. Arner et al., "The Clinical . . .," *Am. J. Optom. & Arch Amer. Acad. Optom.*, vol. 33. No. 8, Aug. 1956.
Kenneth N. Ogle, "Researches in Binocular Vision," Hafner Publishing Co. (N.Y.), 1972.
R. F. J. Mallett, "A Fixation Disparity Test for Distance Use," *The Optician*, vol. 152, No. 3927, 7/8/66.
R. F. J. Mallett, "The Investigation of Heteophoria . . .," *The Optician*, vol. 148, No. 3844, 12/4/64.
F. Hebbard, "Foveal Fixation . . . ," *Am. J. Optom. & Arch Am. Ac. Optom*, vol. 37, No. 1, Jan. 1960.

*Primary Examiner*—Paul A. Sacher
*Attorney, Agent, or Firm*—Gerald L. Smith

[57] ABSTRACT

Apparatus is provided for testing subjects for fixation disparity. The apparatus includes a first sheet-like element having an opening therein which is spaced from the subject being tested. This opening defines the periphery of a target which is dimensioned to represent a fusion stimulus to the subject. Within the opening there are displayed a sequence of paired first and second discrete, parallel target elements which are mutually spaced and fixed a predetermined distance from each other along the parallel lengthwise extends thereof. A sequence of these element pairs are positioned in regularly spaced order about a movable carrier and presented sequentially at the opening in the course of testing. The angular subtense represented by the spacing of the elements is indicated upon the carrier and when the subject perceives that the elements are mutually aligned, a recordation of angular subtense is made and utilized for diagnostic purposes.

10 Claims, 7 Drawing Figures

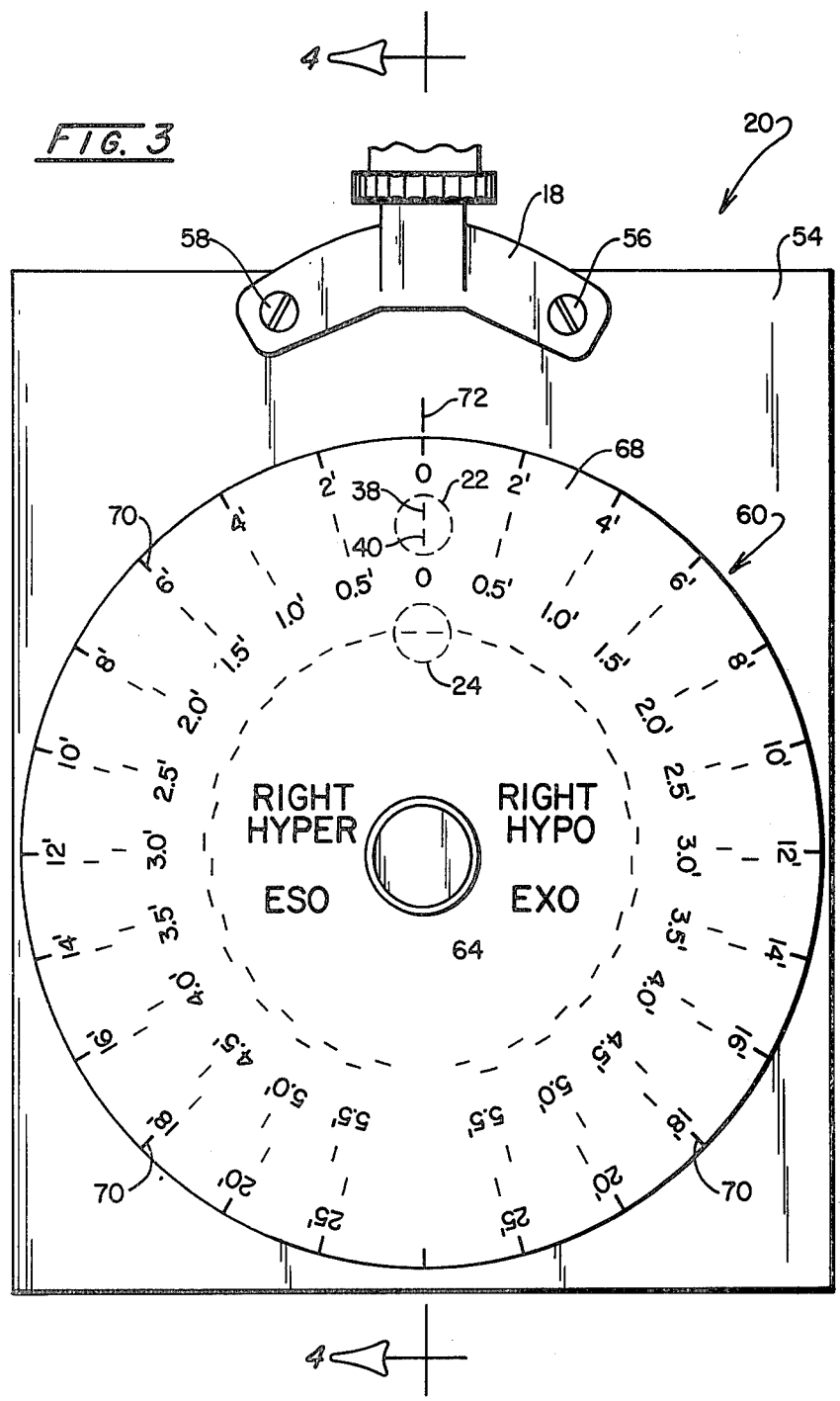

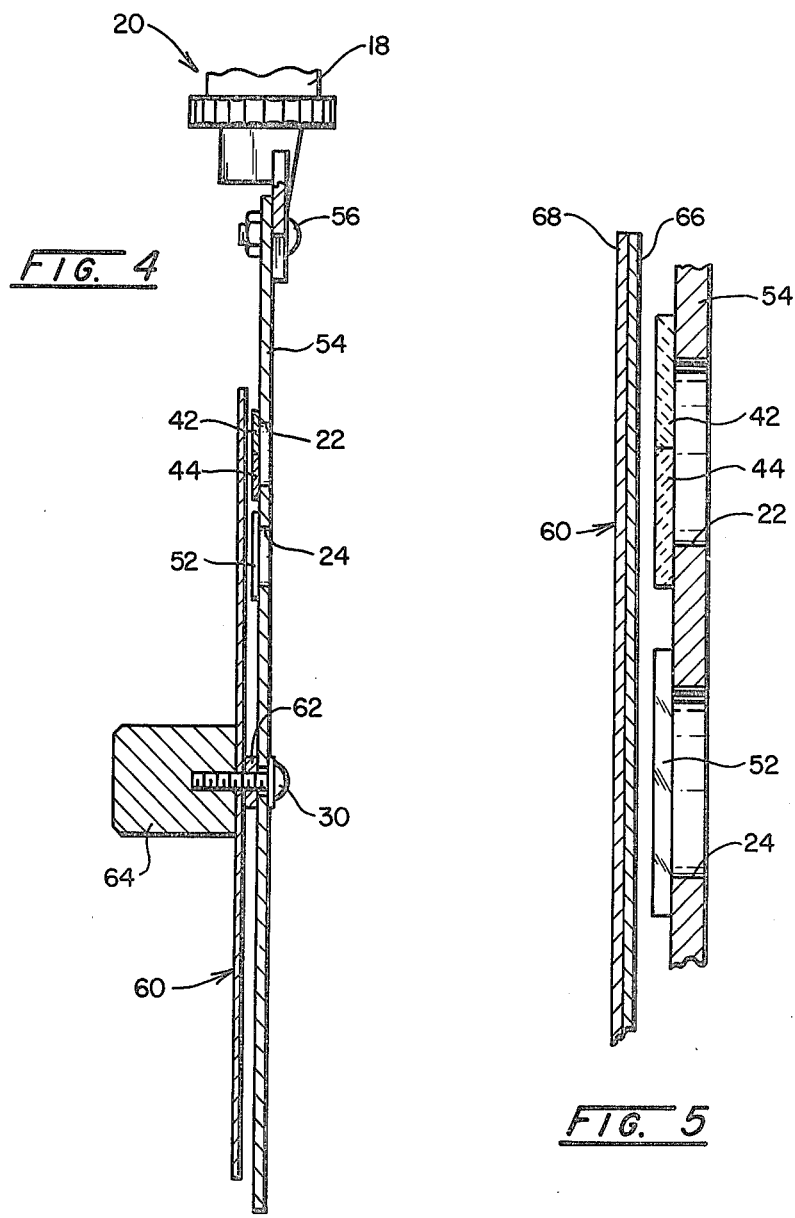

APPARATUS AND SYSTEM FOR ANALYZING FIXATION DISPARITY

This invention was made in the performance of Public Health Service Fellowship 1 F22 EY 01553-01.

BACKGROUND

An individual with normal vision fixates an object or stimulus binocularly and visually responds to it as a single entity. Early in the history of visual science, it was assumed that the visual axes of a person intersect precisely at the point of regard of the viewed object or stimulus to result in a classic stimulation of corresponding retinal elements. For some time, however, investigators have known that the visual axes may be over or under converged and experimentation and observation has been carried out from as early as 1900 to detect the presence of this fixation disparity. In connection with these investigations, reference is made to the following publication:

I. Ogle, K. N., *Researches in Binocular Vision*, Hafner, New York, 1972.

Within certain small limits of such variations or misalignments, a sensory fusion of the monocular images as preceived by each eye still will occur. This small amount of misalignment which is physiologicallly allowed is due to the existence of Panum's fusional area and the angular subtense of the misalignment generally is described as a fixation disparity. Under the phenomenon, the image of the fixation point stimulates disparate retinal elements without diplopia resulting.

Past experimental techniques investigating fixation disparity have looked to an evaluation under both distance and near vision conditions, inasmuch as the oculomotor balance changes for stimuli situated at varying distances from the eye. Distant-vision measurments, for example at about 2.5 meters from a subject's eyes, involved the utilization of a lantern projected central fusable square of about 1.5° visual angle within which short vertical bright lines were located. These lines or arrows were polarized, vertically displaced with respect to each other and movable horizontally at the square to define a variable mutual horizontal displacement. The subject being tested, perceiving the target through a phorometer to which had been attached a pair of Polaroid filters of mutually opposed polarization, observed the arrows at the target which were projected with complementary polarization, so that when viewed by the subject, one line would be seen by one eye and the other with the other eye. By mechanically adjusting the lantern, the displacement of the two arrows was read at that location at which the test subject indicated that the lines appeared to be vertically aligned. The actual physical separation of the lines represented the value of fixation disparity. Test instrumentation for near vision evaluation involved a similar geometry, however a mechanical device provided the two vertical lines, one movable with respect to the other by a mechanical adjustment. For further data concerning such prior test arrangements, reference is made to Publication I above.

Devices generally available in the marketplace for evaluating fixation disparity similarly utilize a polarization technique for effecting the visual isolation of each eye with respect to aligned targets. However, the test mechanisms do not provide an indication of fixation disparity, the test results only indicating the presence or absence of the phenomenon. For a more detailed discourse concerning such instrumentation, reference is made to the following publications:

II. Mallett, R. F. J., A Fixation Disparity Test for Distance Use. The Optician, 1523927,1, July 8, 1966.

III. Mallett, R. F. J., The Investigation of Heterphoria at Near and a New Fixation Disparity Technique, The Optician, 148, 3844–3845, December 1963.

Where an effective and precise evaluation of the amount of disparity is made available, the resultant data can be much more useful to the clinician in a diagnosis of binocular imbalance in the oculomotor system than an indication merely representing the presence or absence of the phenomenon. For fully effective diagnosis, the fixation disparity data must be of sufficient detail with respect to the precise angular extent of misalignment so as to be capable of combination with other clinical indicators or variables of binocular oculomotor balance. For example, an important such combination provides for the development of forced-vergence-fixation-disparity curves. See in this regard:

IV. Ogle, K. N., T. G. Martens, and J. A. Dyer, Oculomotor Imbalance in Binocular Vision and Fixation Disparity, Philadelphia, Lea and Febiger, 1967.

V. Hebbard, F., Foveal fixation disparity measurements and their use in determining the relationship between accommadative convergence and accommodation, Am. J. Optom. Arch. Am. Acad. Optom., 37(1): 3–26, 1960.

As indicated above, presently available devices for analyzing fixation disparity do not develop data suited for full clinical diagnosis, the subject being tested merely observing whether line images perceived in isolation by each eye appear aligned or not. Should the lines appear misaligned to the patient, then ophthalmic prisms are interposed in front of the eyes until the fixation disparity is eliminated. The measurement recorded by this current test is the amount of prism necessary to eliminate the fixation disparity.

Among the additional of the above-mentioned clinical indicators evaluated in the diagnosis of oculomoter balance are heterophoria and vergence. Heterophoria may be evaluated by the Von Graefe method of vertical disassociation. With this method, a target is viewed through a phorometer. With the arrangement, the eyes are disassociated vertically utilizing ophthalmic prisms whereupon double vision is observed. Following this initial procedure, lateral ophthalmic prisms are interposed in the phorometer in incremental amounts until the vertically displaced images appear to be vertically aligned. The resultant evaluation provides data concerning the position of the eyes when there is no stimulus for fusion. Vergence testing is carried out in similar fashion, however, no vertical disassociation is provided, convergent and divergent eye movements elicited by horizontal ophthalmic prisms in small increments to the points of image blur and image break or diplopia, the amount of prism inserted at each point being recorded. Vertical heterophorias and vergences can be similarly measured by changing the prism orientations by 90 degrees.

While the information made available from tests for phoria and vergence remain as valuable diagnostic inputs, considerable value would be promised with a provision of accurate fixation disparity data, in the analysis of oculomotor imbalances. The test instrumentation for carrying out the earlier experimentation required very fine movements of the target lines through the use of micrometers and the like, and, thus, has not found practical introduction into the clinical market as a practical testing procedure.

From the foregoing it may be observed that a need exists for a test method and apparatus which achieves an accurate measurement of the degree of misalignment evoked by a patient's fixation disparity. However, before such apparatus can be made available on a somewhat universal clinical basis, it must be fabricable as well as operable at relatively low cost.

SUMMARY

The present invention is addressed to a method and apparatus for use in determining fixation disparity which provides accurate and efficient readout and which is fabricable at costs commensurate with usage on a wide clinical scale. In using the inventive apparatus, the subject to be tested is positioned at a viewing position spaced a predetermined distance from a fusion stimulus target. At the target there is selectively displayed a sequence of paired, discrete parallel target elements, successive pairs of which are transversely spaced by increasing increments and identified on the apparatus by their corresponding angular subtense. Where the subject observes an alignment of the target elements, the subtense is recorded and utilized in diagnostic procedures. The apparatus is simple, utilizing an indexably rotatable carrier component which may be fabricated photographically and serves to define the linear target elements by rotation behind an opening formed in a display surface or mounting arrangement. A target properly dimensioned to represent a fusion stimulus is provided for use in testing. Inasmuch as the target elements are prefixed upon the carrier, no elaborate mechanism is required to develop the necessary target for display.

Other objects of the invention will, in part, be obvious and will, in part, appear hereinafter.

The invention, accordingly, comprises the method and apparatus possessing the construction, combination of elements and steps which are exemplified in the following detailed disclosure. For a fuller understanding of the nature and objects of the invention, reference should be made to the following detailed description taken in connection with the accompanying drawings.

BRIEF DESCRIPTION OF THE DRAWINGS

FIG. 3 is a rear view of apparatus utilized in accordance with the invention;

FIG. 4 is a sectional view taken through the plane 4—4 of FIG. 3;

FIG. 5 is a more detailed enlarged sectional view of the apparatus of FIG. 4.

DETAILED DESCRIPTION

Figure 1:
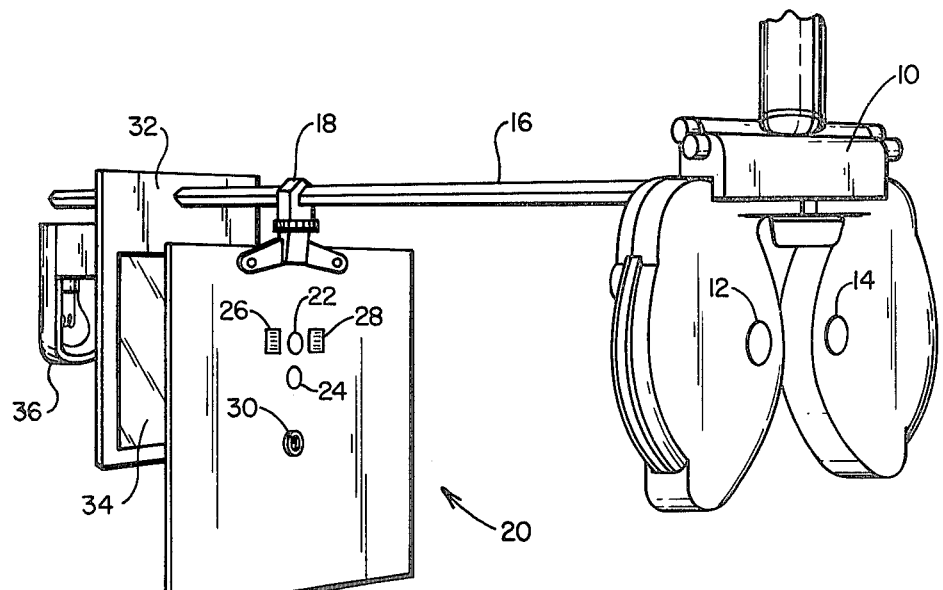
FIG. 1 is a perspective representation of an arrangement for carrying out tests for fixation disparity at near viewing distances.

Refering to FIG. 1, a perspective representation of a test arrangement utilizing the apparatus and method of the invention is provided. The test arrangement makes use of a phoropter 10, a testing device universally available to and used by eye care practitioners. Phoropter 10 incorporates openings 12 and 14 through which the subject being tested looks to perceive testing targets and the like. Further, the phoropter 10 conveniently incorporates polarizing filters which may be positioned within the optics thereof in orientations providing transverse polarization of light rays entering the device and viewed at opening 12 and 14. Such an arrangement permits the use of tests wherein each eye views a separate target element. Extending from the body of phoropter 10 is a horizontally disposed near point rod 16 from which the apparatus of the invention may be suspended. In this regard, a conventional bracket 18 is shown attached to rod 16 for supporting testing apparatus represented generally at 20. The display surface of apparatus 20 facing phoropter 10 includes two openings 22 and 24 the peripheries of which define the outer limits of a fusion stimulus which is observed from the viewing position at openings 12 and 14. On opposite sides of the targets at 22 and 24 are Snellen acuity charts 26 and 28. These charts may, for example, incorporate 20/30 acuity letters. The head of a conventional screw 30 utilized as a pivot axis is in evidence at the display surface. Behind the apparatus 20 is a bracket 32 serving to support a sheet of conventional diffuser material 34 from rod 16. Additionally, a conventional light source 36 is schematically represented as being suspended from rod 16 and oriented for supplying illumination through diffuser 34 to the rearward side of apparatus 20.

The test arrangement shown in FIG. 1 is arranged for testing at near vision distances, a 40 centimeter spacing between the forwardly facing surface of apparatus 20 and the eye position at phoropter 10 being typical. While openings 22 and 24 may have a variety of configurations, preferably, they are made circular as shown and the peripheral extent or diameter of these circles is optionally selected to provide a fusion stimulus and may represent an included angle of about 1.5° as established from the viewing position at openings 12 and 14. Testing for far distances may be carried out utilizing similar devices as at 20, however the dimensioning of the components within the apparatus utilized is enlarged in linear scale fashion.

Figure 2:
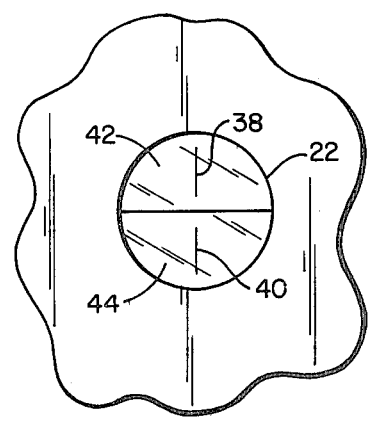
FIG. 2 is a partial view of a target within the apparatus shown in FIG. 1, showing target elements in alignment for testing horizontal deviation forms of fixation disparity.

The target perceived by the test subject at opening 22 for tests carried out to determine fixation disparity in connection with horizontal deviations looks, for an initial setting, as represented in FIG. 2. Note, that the display in that figure shows a pair of discrete, linear target elements 38 and 40 which are positioned respectively behind two transversely oriented sheet polarizers 42 and 44. Elements 38 and 40 are mutually spaced vertically from each other by a fixed distance and are transparent such that light passing through them is perpendicularly polarized with respect to one another. Thus, the subject perceiving the target at 22 through eye positions at 12 and 14 is able to observe only element 38 through one eye and only element 40 through the other eye.

Figure 2A:
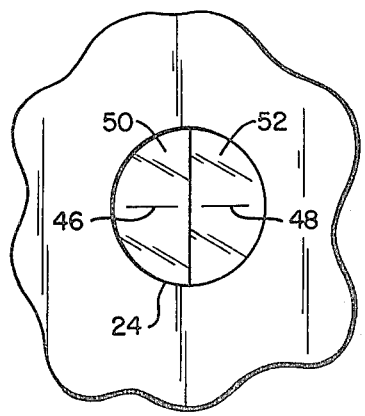
FIG. 2A is another partial view of apparatus of FIG. 1 showing target elements initially presented in measuring vertical deviation forms of fixation disparity.

Looking to FIG. 2A, opening 24 is revealed in closer detail, an initial geometric arrangement of horizontally disposed, parallel linear and mutually spaced target elements 46 and 48 being displayed. Note, that elements 46 and 48 are mutually spaced a fixed distance apart in a horizontal direction, such that each is located behind a respective sheet polarizer 50 and 52. Thus, the arrangement of FIG. 2A is similar to that of FIG. 2, however, the geometric orientation of the target elements 46 and 48 are the initial ones utilized in carrying out vertical deviation type fixation disparity testing.

Turning to FIGS. 4 and 5, the construction of apparatus 20 is revealed in more detail. FIG. 4 shows that the apparatus 20 includes a display component 54 which may be present as a relatively thin rigid sheet of polymeric material and which is bolted to bracket 18 by bolts and nuts as at 56 and 58. The figure shows that the sheet polarizers 42 and 44 are attached to the back surface of component 54. Polarizer sheets 52 and 50 similarly are attached, for instance utilizing a glue adhering medium or the like, only one such sheet polarizer being shown at 52 in view of the altered orientation thereof.

Note, that upon component 54, at the rearward side thereof, is a target element carrier 60. Carrier 60 is configured having a circular periphery and is rotationally mounted at the center of such circular periphery by screw 30 which extends through component 54, thence through a spacer washer 62, thence through carrier 60 and into a knob 64. With such mounting, the operator, carrying out testing, can simply rotate carrier 60 by hand between successive indexing positions in the manner described hereinafter.

Figure 6:
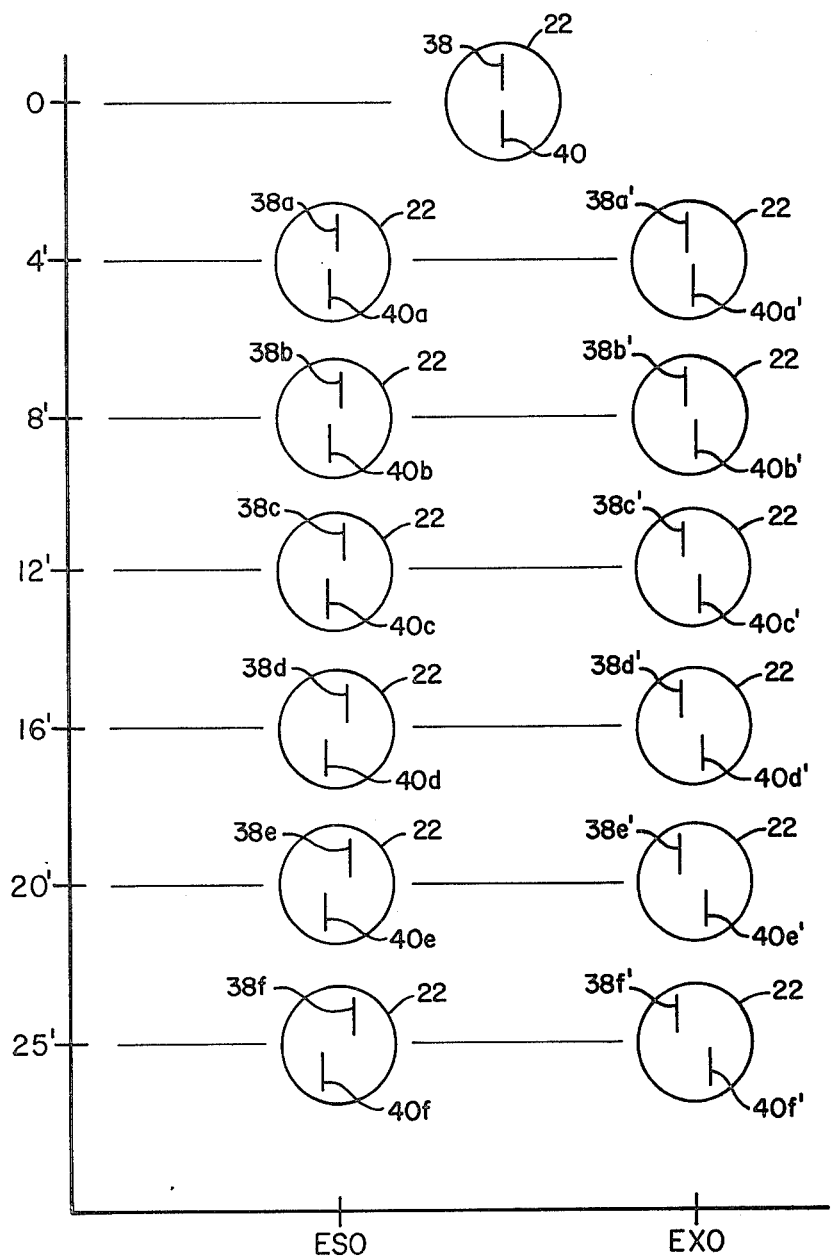
FIG. 6 is a diagramatic representation of the geometric orientations of target elements used in determining horizontal deviation type fixation disparity, such geometric arrangements being utilized in the apparatus of the invention.

Looking additionally to FIG. 3, the circular periphery and laminar structure of carrier 60 is revealed. FIG. 5 shows that the laminar structure of the carrier includes a forwardly disposed thin polymeric transparent sheet 66 to which is joined a thin translucent sheet 68, which may be present as white paper or the like. FIG. 3 shows that sheet 68, in addition to serving a light diffusing function as described later herein, also carries a succession of regulary spaced index marks certain of which are identified at 70. Indicia representing angular minutes corresponding with the angular subtense of the spaced target elements both for those elements displayed at opening 22 and those elements displayed at opening 24 also are printed upon sheet 68. An aligning index mark 72 is positioned upon the rearward face of component 54 at a location coincident with a radius extending from the point of rotation of component 60 and passing through the center of openings 22 and 24. Thus, the operator may turn knob 64 to locate component 60 at any of a sequence or series of regularly spaced positions defined by index marks 70. Note, that two sequences of angular designations are indicated on surface 68 for each of the target openings 22 and 24. The target elements for each of the angular designations are formed within polymeric sheet 66 and, in a preferred embodiment, are transparent such that light passing through diffuser 34 and translucent sheet 68 will create appropriate target line images at openings 22 and 24 having been perpendicularly polarized with respect to one another by the earlier described polarizer sheets. The outermost ones of the pairs of the target lines appear generally vertically oriented within opening 22 when positioned thereat and are intended to effect a measurement of horizontal fixation disparity. Looking additionally to FIG. 6, an exemplary compilation of a sequence of incrementally increasing transversely spaced elements as presented at opening 22 is shown. The angular subtense is indicated for each representation and these representations are provided in four minute increments in order to more clearly show that the spacing between elements 38 and 40, as represented in the sequence (38a, 40a)–(38f, 40f) increases incrementally. The geometric orientations for the sequence are representative of a succession of spacings intended for determining eso fixation disparities. Conversely, the sequence of target elements (38a', 40a')–(38f', 40f') are representative of those utilized in defining a succession of exo fixation disparities. A similar sequence of geometric orientations of target elements for testing vertical deviation, as described in connection with FIG. 2A, would be observed to be quite similar to that shown if FIG. 6 when observed in a horizontal orientation. As shown in FIG. 3, the sequences for eso and exo fixation disparities are labeled about a circumference of carrier 60 in respective counterclockwise and clockwise directions and similarly, hyper and hypo disparity fixation indications are shown printed circumferentially inwardly from the eso and exo designations.

The term "angular subtense" of the fixation disparity as used herein is intended to mean the angle which the perpendicular transverse separation of the target elements subtends at the point which is midway on a line between the centers of the entrance pupils of the subjects eyes.

Target element carrier 60 is readily fabricated, the indicia and markings on outer sheet 68 being printable, while the target element lines described above may be photographically formed within sheet 66. In the latter regard, drawings of the linear elements with appropriate mutual spacings may be made in black pigment upon white paper. The resultant drawings then may be photographed to provide a positive transparency which is positioned upon a white or clear carrier which, in turn, is photographed to develop an opaque (negative) sheet having transparent openings therein serving to provide the sequences of paired target elements. Sheets 66 and 68 of carrier 60 are readily laminated together utilizing a variety of techniques including the packaging thereof within a thin transparent material.

The method for carrying out tests for fixation disparity with apparatus 20 provides for positioning the subject, i.e. patient to be tested at the viewing station, i.e. at phoropter 10. Acuity charts as at 26 or 28 then are utilized to assure that the eyes of the subject are focused at the forward surface of apparatus 20 and, particularly, at the fusion stimulus presented at a selected opening 22 or 24. Carrier 60 initially is oriented such that the 0 minutes orientation of target elements is aligned with index 72 and the line geometry described in connection with FIGS. 2 and 2A is presented at respective openings 22 and 24. The subject is requested to look at the target, for example at opening 22 and advise the operator whether or not elements 38 and 40 are perfectly vertically aligned. If the subject indicates that they are not, the question is asked whether the top element 38 is to the right or left of the bottom element 40. This information indicates to the operator which direction, eso or exo, carrier 60 should be rotated. Different presentations are made to the subject until such time as the target elements appear to be aligned vertically at opening 22. These presentations are made to bracket the subject's responses. The offset associated with a perceived alignment is used as the measure of fixation disparity. This measure initially is obtained with no prism within the optics of phoropter 10. Following this initial determination, similar measurements of fixation disparity are made with the addition of prisms (base-in and base-out) in small, i.e. three diopter increments, until fusion can no longer be held by the subject i.e. dipolpia or double vision is evidenced. Data thus derived then is used to plot forced-vergence fixation-disparity curves in the manner described in publications IV and V.

Similar tests are carried out for vertical deviation utilizing the earlier-described horizontally oriented linear target elements as presented at opening 24.

The testing method provided with the apparatus can be quite useful in the diagnosis of binocular imbalances in the oculomotor system. Several research efforts have indicated this usefulness, as represented by the following publications which are incorporated herein by reference:

VI. Sheedy, J. E., and Saladin, J. J., Phoria, Vergence, and Fixation Disparity in Oculomotor Problems, Am. J. Opt. and Physiol. Optics 54, 474–478, 1977.

VII. Sheedy, J. E., and Saladin, J. J., Association of Symptoms with Measures of Oculomotor Deficiencis. Am. J. Opt. and Physiol. Optics.

VIII. Saladin, J. J., and Sheedy, J. E., A Population Study of Relationships Between Fixation Disparity, Heterophorias, and Vergences. Am. J. Opt. and Physiol. Optics.

IX. Arner, R. S., Berger, S. I., Braverman, G., and Kaplan, M. The Clinical Significance of the Effect of Vergence on Fixation Disparity., Am. J. Opt. and Arch. Am. Acad. Opt. 33, 399, 1956.

As is apparent, apparatus 20 can be fabricated at low cost, thus permitting its broad availability for clinical utilization. While the apparatus has been described utilizing polarizing filters for purposes of isolating the viewing of target images for each eye, it will be apparent that other illumination systems can be utilized to achieve the same result. For example, shutters may be operated in conjunction with the target and viewing station, anaglyphic color coding may be utilized, as well as directional optical channels.

Since certain changes may be made in the above described method and apparatus without departing from the scope of the invention herein involved, it is intended that all matter contained in the description thereof or shown in the accompanying drawings shall be interpreted as illustrative and not in a limited sense.

What is claimed is:

1. Apparatus for use in determining fixation disparity in the vision of a human subject for a fusion stimulus situated a predetermined distance from the eyes of said subject comprising:

display means positionable for viewing a forwardly disposed surface thereof by said subject at said predetermined distance and configured having a target defining opening extending therethrough of predetermined fusible peripheral extent;

target element carrier means mounted for movement upon said display means opposite said forwardly disposed surface thereof, formed of thin sheet material and configured to carry a sequence of pairs of discrete linear first and second target elements mutually spaced a fixed predetermined distance from each other along the parallel lengthwise extent thereof, said sequence commencing with a first pair of said elements arranged in end-to-end relationship and successive said element pairs being spaced apart transversely to said lengthwise parallel extent by predetermined incrementally increasing amounts, each said transverse spacing corresponding with the angular subtense of said spaced first and second elements witnessed at the eyes of said subject for said predetermined distance; and means for illuminating said target in a manner wherein one eye of said subject perceives only said first element of a said pair when within said opening while the opposite eye perceives only the second said element of said pair.

2. The apparatus of claim 1 in which said target element carrier means is configured to carry first and second sequences of said pairs of first and second elements, the parallel lengthwise extents of which are arranged to be vertically oriented when at said opening, said transverse spacings of said first sequence being selected to define a succession of exo fixation disparities, said transverse spacing of said second sequence being selected to define a succession of eso fixation disparities.

3. The apparatus of claim 2 in which:

said display means is configured having a second target defining opening extending therethrough of predetermined fusible peripheral extent; and said target element carrier means is configured to carry third and fourth sequences of pairs of discrete linear third and fourth elements mutually spaced a fixed predetermined distance from each other along the parallel lengthwise extent thereof, said third and fourth sequences commencing with a first pair of said third and fourth elements arranged in end-to-end relationship, and successive said third and fourth element pairs being spaced apart transversely to said lengthwise parallel extent by predetermined incrementally increasing amounts, each said transverse spacing corresponding with the angular subtense of said spaced third and fourth elements witnessed at the eyes of said subject for said predetermined distance, said parallel lengthwise extents of said third and fourth elements being arranged to be horizontally oriented when positioned at said second target defining opening, said transverse spacings of said third sequence being selected to define a succession of hyper fixation disparities, said transverse spacings of said fourth sequence being selected to define a succession of hypo fixation disparities.

4. The apparatus of claim 1 in which:

said target element carrier means comprises a sheet of material generally opaque to light, said first and second target elements being present as light transmitting regions thereof; and said illuminating means includes a first light polarizing filter mounted over a portion of said opening to an extent polarizing light transmitted through each said first element when positioned at said opening, and a second light polarizing filter positioned over a portion of said opening in a manner polarizing perpendicular with respect to said first filter light transmitted through each said second element when positioned at said opening.

5. The apparatus of claim 1 in which said target element carrier means is configured for carrying said pairs of first and second elements in regularly spaced geometric alignment about a circumference of a circle, said carrier being mounted upon said display means for rotation about the center of said circle.

6. The apparatus of claim 5 in which said target element carrier means includes indicia identifying each said angular subtense of said paired target elements.

7. The method for measuring fixation disparity in a human subject comprising the steps of:

positioning said subject in a manner wherein the eyes thereof are spaced a predetermined distance from a target dimensioned to represent a fusion stimulus to said subject;

displaying as a portion of said target a sequence of paired, first and second discrete, linear parallel target elements carried upon a support, mutually spaced a fixed predetermined distance from each other along the parallel lengthwise extent thereof, said sequence commencing with a first pair of said first and second elements mutually arranged in parallel end-to-end relationship and successive said element pairs fixed upon said support being spaced apart transversely to said lengthwise parallel extent by predetermined incrementally increasing amounts, each said transverse spacing corresponding with the angular subtense of said spaced elements witnessed at said subject eyes, said sequential display being carried out by moving said support to provide successive presentations of said pairs at said target;

effecting an observation by said subject of said target in a manner wherein one eye thereof perceives only said first element of said pair while the opposite eye perceives only the second said element thereof;

determining that element pair which said subject perceives at said target as being aligned in parallel, end-to-end relationship;

indicating the value of said angular subtense corresponding with said transverse spacing of said element pair perceived as being aligned in parallel, end-to-end relationship, said angle representing fixation disparity.

8. The method of claim 7 wherein said observation is effected by illuminating said first and second elements at said target with respective mutually transversely polarized light; and interposing correspondingly transversely polarizing filter means before the eyes of said subject.

9. The method of claim 7 wherein said successive first and second element pairs are formed in a circular pattern upon said support, and said movement thereof is rotational in one direction to determine exo fixation disparities and in an opposite direction to determine eso fixation disparities.

10. The method of claim 7 wherein said subject is positioned at the phoropter and said target is mounted upon the near point rod thereof.

* * * * *